United States Patent
Malin et al.

(10) Patent No.: US 6,623,972 B2
(45) Date of Patent: Sep. 23, 2003

(54) AUTOMATED METHOD FOR DETECTING, QUANTIFYING AND MONITORING EXOGENOUS HEMOGLOBIN IN WHOLE BLOOD, PLASMA AND SERUM

(75) Inventors: Michael J. Malin, South Nyack, NY (US); Phyllis Shapiro, Stamford, CT (US)

(73) Assignee: Bayer Corporation, Tarrytown, NY (US)

( * ) Notice: Subject to any disclaimer, the term of this patent is extended or adjusted under 35 U.S.C. 154(b) by 285 days.

(21) Appl. No.: 09/861,069

(22) Filed: May 18, 2001

(65) Prior Publication Data

US 2002/0012904 A1 Jan. 31, 2002

Related U.S. Application Data

(60) Provisional application No. 60/210,625, filed on Jun. 9, 2000.

(51) Int. Cl.[7] ............................................. G01N 33/72
(52) U.S. Cl. ........................... 436/66; 436/63; 436/164; 435/2
(58) Field of Search ............................ 436/63, 66, 164; 435/2

(56) References Cited

U.S. PATENT DOCUMENTS 5,416,026 A * 5/1995 Davis ........................... 436/66
5,858,794 A * 1/1999 Malin ........................... 436/66

FOREIGN PATENT DOCUMENTS

WO   WO 98/39634   9/1998   .......... G01N/21/27

OTHER PUBLICATIONS

S.K. Ritter, May 18, 1998, "Passing A Blood Test", Science/Technology, Chemical and Engineering News, pp. 37–44.
S. Yanchinski, Jun. 1, 1998, "Hemolink Moves to U.S. Phase III", Canada Watch, Genetic Engineering News, pp. 20–21.
E. Bucci et al., 1989, J. Biol. Chem., 264:6191–6195.
T. Standl et al., 1998, Br. J. Anaesth., 80:189–194.
J.W. Freytag et al., 1998, Red Blood Cell Substitutes, 325–333.
J.G. Adamson et al., 1998, Red Blood Cell Substitutes, 335–351.
D.J. Nelson, 1998, Red Blood Cell Substitutes, 353–400.
J.H. Seigel et al., 1998, Red Blood Cell Substitutes, 119–164.
M. Malin et al., 1989, Am. J. Clin. Pathol., 92:286–294.
M. Malin et al., 1992, Anal. Chim. Acta, 262:67–77.
Kim and Ornstein, 1983, Cytometry, 3:419–427.
Tycko et al., 1985, Appl. Optics, 24:1355–1365.
Mohandas et al., 1986, Blood, 68:506–513.

* cited by examiner

Primary Examiner—Maureen M. Wallenhorst
(74) Attorney, Agent, or Firm—Morgan & Finnegan, LLP

(57) ABSTRACT

The invention provides a new method and system for detecting and monitoring extracellular or exogenously added hemoglobin, i.e., a cell-free hemoglobin substitute or derivative, in a blood, plasma, or serum sample of an individual, particularly a whole blood sample. The invention further describes the use of automated hematology analyzers to determine and quantify at the same time the concentration of total, cellular and exogenous hemoglobin in a blood, plasma, or serum sample, and is particularly advantageous for medical use during or after patient trauma or surgery, as well as for monitoring hemoglobin levels during patient recovery.

31 Claims, No Drawings

AUTOMATED METHOD FOR DETECTING, QUANTIFYING AND MONITORING EXOGENOUS HEMOGLOBIN IN WHOLE BLOOD, PLASMA AND SERUM

This application claims benefit of patent application U.S. Ser. No. 60/210,625, filed Jun. 9, 2000.

FIELD OF THE INVENTION

The present invention relates generally to new methods and systems for detecting, quantifying and monitoring extracellular or exogenously added hemoglobin, including hemoglobin substitutes, in a blood sample, particularly a whole blood sample, as well as in plasma and serum samples. The present invention further relates to the use of automated hematology analyzers to determine and quantify the concentration of extracellular and exogenous hemoglobin, including cell-free hemoglobin substitutes, in a blood, plasma, or serum sample, and is particularly advantageous for medical use during patient trauma or surgery, as well as for monitoring hemoglobin levels during recovery.

BACKGROUND OF THE INVENTION

Whole blood substitutes have long been sought after as alternatives to whole blood for use in the medical field, particularly following trauma and/or surgery where transfusions are needed. Motivated by the need to supply large quantities of blood to the military on the battlefield, but limited by the resources to insure the safety of the blood supply in the face of contamination by human pathogens and viruses, notably hepatitis viruses and HIV, blood banks abandoned their whole blood supply programs in the early 1980s. However, the search for blood substitutes, e.g., synthetic blood substitutes, that are free of contaminants and that can be used in patient treatment has continued.

Currently, there is a renewed interest to produce and/or isolate a blood substitute. However, because of the complexity of blood and the various components that comprise whole blood, as well as the stringent federal regulations governing the testing and use of such synthetic products, industry has focused its research efforts on the development of products which temporarily deliver oxygen, rather than on the development of a variety of different products having other functions that transfused blood provides.

Hemoglobin (HGB) isolated from human or animal blood, or a synthetically produced oxygen carrier, such as perfluorocarbon, are two types of hemoglobin substitutes that are currently in clinical trials. Other red blood cell substitutes, i.e., oxygen-carrying hemoglobin substitutes, have also been developed and characterized for use in patients. (See, for example, *Red Blood Cell Substitutes,* 1998, (Eds.) A. S. Rudolph, R. Rabinovici, and G. Z. Feuerstein, Dekker, New York, N.Y.). Such oxygen-carrying hemoglobin substitutes may be used in conjunction with standard medical therapies, such as transfused blood or blood products.

As a specific but nonlimiting example, Enzon, Inc. (Piscataway, N.J.), has developed a polyethylene glycol (PEG)-modified bovine hemoglobin, abbreviated PEG-HGB. PEG-HGB is produced by a process in which strands of PEG are crosslinked to the surfaces of HGB molecules, for example, as disclosed in U.S. Pat. Nos. 5,386,014 and 5,234,903 to Nho et al.). Other specific, yet nonlimiting, examples include Hemopure® and Oxyglobin (Biopure, Cambridge, Mass.).

The first generation HGB substitutes were generally intended for short term treatment of blood/oxygen loss during surgery or following trauma. One disadvantage of HGB substitutes is the short circulation half-life attributed to these products. For example, HGB substitutes that are added to blood have a circulation half-life of up to 36 hours compared with a circulation half-life of up to 30 days for transfused blood. However, this relatively short half-life is typically not a serious problem associated with the use of such blood substitutes, because these products are predominantly indicated for short-term treatment objectives.

In determining whether or not to transfuse a patient who has a low blood hemoglobin concentration, the transfusion "trigger" is between about 6 and 8 g/dL of hemoglobin in whole blood and depends on a number of specific factors, such as blood volume status, pulmonary, cardiac and cerebrovascular status, chronicity or severity of anemia, patient symptoms relating to blood loss, expected blood loss for a particular procedure, risk of re-bleeding from surgery, high risk patients (i.e., the elderly), and thrombocytopenia.

In general, the measurement of hemoglobin in whole blood samples is performed by commercially available automated hematology analyzers. To date, with the exception of certain hematology analyzers, such as those available from Bayer Corporation, e.g., the ADVIA 120® hematology analyzer system, other commercially-available blood analyzers are able to measure only total hemoglobin, which includes not only exogenously added hemoglobin, but also intracellular hemoglobin that is derived from the red blood cells in a blood sample. The present invention provides the ability to determine and measure exogenous hemoglobin in a whole blood, plasma, or serum sample in a reliable, reproducible and automated way.

SUMMARY OF THE INVENTION

It is an object of the present invention to provide automated methods and hematology systems to specifically and accurately detect, quantify and monitor different types of hemoglobin in a blood, plasma, or serum sample, preferably a whole blood sample, undergoing analysis, namely, (i) hemoglobin derived from red blood cells (i.e., intracellular hemoglobin, or cellular hemoglobin, as used herein); (ii) extracellular hemoglobin, or a hemoglobin product or substitute, particularly, a cell-free hemoglobin derivative, e.g., PEG-HGB, or a synthetic form of hemoglobin, e.g., Hemopure®, (Biopure, Cambridge, Mass.); Oxyglobin, (Biopure, Cambridge, Mass.), which has been transfused into a patient requiring added HGB, or otherwise added to a blood, plasma, or serum sample (i.e., exogenous hemoglobin); and (iii) total hemoglobin (i.e., the combination of intracellular and exogenous hemoglobin).

It is another object of the present invention to provide the ability to monitor, during a course or regimen of treatment, hemoglobin or a hemoglobin product, derivative or substitute, such as a cell-free hemoglobin derivative, that has been added to blood of a patient or individual in need thereof. Also, in accordance with the present invention, hemoglobin, or a hemoglobin product, derivative or substitute, such as a cell-free hemoglobin derivative, can be monitored, determined or quantified as exogenous hemoglobin in a patient's blood, plasma, or serum, after the patient has been transfused with such a hemoglobin product, or a substance containing the product (e.g., a physiologically acceptable solution or composition, and the like).

It is yet another object of the present invention to provide a system to differentiate and accurately measure the contribution of an added or exogenous hemoglobin product or blood substitute, e.g., PEG-HGB, separately and distinctly from the contribution of cellular HGB which derives from a patient's red blood cells. In accordance with the present invention, the automated analytical method and system as described calculate a specific concentration of the extracellular hemoglobin in a blood sample which has been transfused with a hemoglobin product, or in a blood, plasma, or serum sample which contains extracellular hemoglobin to be detected. Thus, the invention allows the detection and monitoring of an extracellular hemoglobin component, even in the presence of a cellular hemoglobin component derived from the red blood cells in a given sample. In addition, through the present method, as little as about 0.5 g/dL of hemoglobin is detectable in a total of approximately 6.0 g/dL of extracellular hemoglobin. Experiments were performed in the HGB concentration range which is relevant to transfusions, i.e., a decision point of about 6–7 g/dL of total HGB in blood. Moreover, hemoglobin was recoverable and quantified in blood samples that were 24 hours old, and which had been stored at temperatures of 2° C. to 8° C.

Further objects and advantages afforded by the present invention will be apparent from the detailed description hereinbelow.

DETAILED DESCRIPTION OF THE INVENTION

The present invention provides automated methods and hematology systems to specifically and accurately detect and quantify different types of hemoglobin in a whole blood, plasma, or serum sample. Automated hematology analyzers produced by and commercially available from Bayer Corporation, the assignee hereof, have been found to be able to directly determine and measure the concentration of exogenous, i.e., extracellular, hemoglobin in a sample. Suitable instruments for carrying out the analyses of the present invention possess two analytic channels which measure the concentration of hemoglobin in a blood sample. Specifically, and by way of example, the Bayer H*™ series of hematology analyzer instruments and the Bayer ADVIA® series of hematology analyzer instrument systems (e.g., ADVIA 120®), as well as hematology analyzers with similar design or function, have the capability of performing quantitative analysis on the hemoglobin content of blood, plasma and serum which contain exogenous hemoglobin.

Other commercially available blood analyzers currently measure only total hemoglobin (i.e., the combination of cellular HGB and extracellular, exogenously added HGB) in a blood sample. However, the automated hematology instruments for use in the present invention, e.g., the above-mentioned Bayer hematology analyzers, are able to determine separately and independently the cellular HGB (reported as "Calculated HGB"), as well as total hemoglobin (reported as "HGB") in a whole blood sample. To date, currently available hematology analyzers cannot simultaneously detect cellular hemoglobin and non-cellular hemoglobin, i.e., exogenously added hemoglobin, in a whole blood, plasma, or serum sample, and thus, cannot report the separate values of these measurements.

In addition, the monitoring of patient progress in those patients who have received exogenous hemoglobin, e.g., PEG-HGB, or a cell-free, oxygen-carrying hemoglobin substitute, such as Hemopure® or Oxyglobin (Biopure, Cambridge, Mass.) via transfusions, for example, is not possible with other commercially available analyzers, because these analyzers are not able to distinguish between the hemoglobin contributed by the exogenously provided HGB substitute and the hemoglobin contributed by the red blood cells in a whole blood sample, particularly in the cases of acute blood loss or autolysis.

In contrast to presently-used blood analyzers, the automated analyzers and methods according to the present invention can differentiate and accurately measure the contribution of an exogenous HGB substitute separately and distinctly from the contribution of cellular HGB derived from red blood cells. As described herein, the automated analyzers calculate a specific concentration of the extracellular hemoglobin in a whole blood, plasma, or serum sample which has been transfused with a hemoglobin product, thereby allowing the detection and monitoring of exogenous hemoglobin in the absence of the cellular hemoglobin component derived from the red blood cells in a given sample. In addition, the analyzers described herein provide cellular and total hemoglobin values for a blood sample containing an added hemoglobin product.

The present invention is particularly advantageous because a number of cell-free hemoglobin derivatives have been developed for use instead of whole blood, especially in trauma cases. Thus, the present invention provides a viable method for determining, measuring and monitoring levels of such hemoglobin products in blood, plasma or serum when such products have been added exogenously to blood, and introduced (e.g., transfused) into patients as a substitute for whole blood.

It will be appreciated that the method of the present invention embraces the analysis of blood samples, preferably whole blood samples, as well as plasma and serum samples, from patients who have received cell-free red blood cell substitutes, i.e., who have added hemoglobin or oxygen-carrying blood substitute products in their blood, for a variety of medical reasons. It will be further appreciated that there are a number of cell-free, hemoglobin-based red blood cell substitutes which can be added to blood, or used as blood substitutes, to treat patients requiring such red blood cell or oxygen-carrying blood substitutes, for various therapies and treatment conditions, such as transfusion, restoration of blood volume, treatment of acute blood loss, surgery, shock (e.g., hemorrhagic shock), or tumor oxygenation, for example.

Nonlimiting examples of cell-free, hemoglobin-based red blood cell substitutes, or oxygen-carrying substitutes, that can be determined, measured, and/or monitored in whole blood, plasma, or serum samples in accordance with the present methods include cross-linked, particularly chemically cross-linked, human hemoglobin products (e.g., D. J. Nelson, 1998, "HemAssist: Development and Clinical Profile", In: *Red Blood Cell Substitutes*, 1998, (Eds.) A. S. Rudolph, R. Rabinovici, and G. Z. Feuerstein, Dekker, New York, N.Y., pp. 353–400; J. Adamson et al., 1998, *Ibid.,* pp. 335–351; and T. M. S. Chang, 1998, *Ibid.,* pp. 465–473); recombinant hemoglobin products, particularly recombinant human hemoglobin (e.g., J. H. Siegel et al., 1998, *Ibid.,* pp. 119–164 and J. W. Freytag and D. Templeton, 1998, *Ibid.,* pp. 325–222) or recombinant bovine hemoglobin; purified, preferably ultrapurified, animal hemoglobin products, e.g., ultrapurified bovine hemoglobin and ultrapurified human hemoglobin; and animal-based oxygen-carrying products, for example, bovine hemoglobin-based oxygen carrier (HBOC) products, e.g., "Hemopure®" and oxyglobin (Biopure, Cambridge, Mass.); (W. R. Light et al., 1998, *Ibid.,* pp. 421–436; T. Standl et al., 1998, *Br. J. Anaesth.,* 80(2):189–194; and Palaparthy et al., 2000, *Adv. Drug Delivery Reviews,* 40:185–198). The purified or ultrapurified hemoglobin products are cell-free and can be cross-linked or polymerized, e.g., Hemopure® and Oxyglobin, (Biopure, Cambridge, Mass.).

The use of automated hematology analyzers in the methods according to the present invention provides further advantages, which are described herein and demonstrated by the Examples as set forth below. More specifically, and by way of example, the use of automated hematology analyzer analysis according to this invention allows the detection and measurement of extracellular (or non cell-derived) PEG-HGB (e.g., $\geq 0.2$ to 5.6 g/dL of blood) that is added to anticoagulated whole blood samples. The recovery of PEG-HGB is linear (e.g., $\geq 0.2$ to 5.6 g/dL of blood) when added to plasma or whole blood samples. Also, PEG-HGB is recoverable in 24 hour old samples that have been stored at 2–8° C. In addition, the bovine hemoglobin products, Hemopure (Biopure, Cambridge, Mass.) and Oxyglobin, also obtained from Biopure, have been added to whole blood and plasma samples and accurately detected as oxygen-carrying blood substitutes according to the methods of the present invention. (Examples 5 and 6).

The added HGB component in a blood sample is obtained by determining the difference between the total HGB (computed from the calorimetric absorbance in the hemoglobin channel of the hematology analyzer) and the calculated cellular HGB (derived from the red blood cell (RBC) cytogram in the red cell channel of the hematology analyzer), which is calculated by the formula: (RBC×MCV× CHCM/1000), where MCV is mean cell volume and CHCM is Cellular Hemoglobin Concentration Mean, which measures the same cellular property as MCHC, or Mean Cellular Hemoglobin Concentration, in unlysed blood. The CHCM value is obtained from the Red Blood Cell channel of the hematology analyzer, such as the ADVIA 120® hematology system.

In particular, CHCM is obtained from light scattering measurements according to Mie Theory (see Tycko et al., 1985, *Appl. Optics*, 24:1355–1365, and U.S. Pat. No. 4,735,504 to Tycko). In contrast, MCHC is obtained by dividing total HGB by the product (MCV×RBC). Practically speaking, MCHC is not exactly equal to CHCM for normal blood samples, but these values preferably agree closely. For example, the MCHC value associated with the added hemoglobin component is preferably within a range of about 0–5 g/dL of blood, more preferably between about 0–2 g/dL of blood, of the CHCM value. The difference between total hemoglobin and intracellular hemoglobin is termed "HGB Delta" ("HGBΔ") and represents the concentration of exogenously added hemoglobin, e.g., PEG-HGB, in a blood sample.

An explanation related to the above-mentioned lack of complete equality between the MCHC and CHCM values is as follows. After a typical meal, for example, it is not uncommon for the blood plasma to develop a small degree of lipemia (i.e., a suspension of small submicroscopic and microscopic particles of lipids, called chilomicrons). The presence of the particles causes a minor amount of light scattering, thereby diminishing the amount of light transmitted through a solution of hemoglobin in a hemoglobinometer. Consequently, the solution appears to contain slightly more hemoglobin than it actually does. The cell by cell measurements of hemoglobin concentration, performed by the Bayer ADVIA 120® hematology analyzer, are free of this error. The ADVIA 120® is calibrated such that if ΔHGB is greater than 1.9 gm/dL, a sample is flagged as abnormal; i.e., a degree of lipemia in excess of this amount is considered abnormal. Also, if part of the blood sample has hemolysed, either in vivo in the patient or in the collection tube, a ΔHGB value is also produced. The two HGB measurements performed by the ADVIA 120® analyzer alert the physician or clinician to the existence of any abnormal lipemia or hemolysis in a patient sample.

Until the present invention, no other commercially available automated hematology analyzer was able to detect simultaneously the intracellular (or cellular) hemoglobin ("Calculated HGB") and extracellular HGB (HGBΔ) in a whole blood sample. Accordingly, the present invention provides the ability to monitor added hemoglobin substitutes to blood by determining the amount of added hemoglobin substitute independently of the hemoglobin contributed by the red blood cell component of blood. For normal unlysed, and for abnormal blood samples, with a properly calibrated system, HGB Delta equals zero.

In accordance with an embodiment of the present invention, the hematology analyzers suitable for use in the present invention, e.g., Bayer ADVIA 120® and the Bayer H*™ System series of hematology analyzers, are able to directly measure the concentration of exogenous extracellular hemoglobin because these instruments possess two analytic or detection channels, each of which measures a different type of hemoglobin concentration in a whole blood or plasma sample.

In such instruments, one of the analytic or detection channels is the Hemoglobin (HGB) channel which measures the concentration of total hemoglobin in the sample by means of hemolysis and extraction of the hemes from their biological complex with globin, forming a ligated ferric heme species which is captured in a surfactant micelle and is measured spectrophotometrically (See, for example, U.S. Pat. No. 5,858,794 to M. Malin; M. Malin et al., 1992, *Anal. Chim. Acta*, 262:67–77; and M. Malin et al., 1989, *Am. J. Clin. Path.*, 92:286–294). The second analytic or detection channel in such instruments is the Red Blood Cell (RBC) channel which measures the red blood cell concentration and the mean cell volume (MCV) and mean cell hemoglobin concentration (MCHC) of approximately 10,000 individual erythrocytes as they pass through two light scattering detectors.

The presence and design of hematology analyzers having both an HGB channel and an RBC channel, in conjunction with two light scattering detectors which detect the light scattered on a cell-by-cell basis as a blood sample containing RBCs passes through the RBC optical channel, allow a difference between intracellular hemoglobin and extracellular hemoglobin to be determined and calculated, thereby providing the performance of the method described herein. For a description of the optical mechanisms of suitable automated analyzers that are capable of performing the method of the present invention, see Kim and Ornstein, 1983, *Cytometry*, 3:419–427; U.S. Pat. No. 4,412,004 to Ornstein and Kim; Tycko et al., 1985, *Appl. Optics*, 24:1355–1365; U.S. Pat. No. 4,735,504 to Tycko; and Mohandas et al., 1986, *Blood*, 68:506–513.

As a specific but nonlimiting example, the Bayer ADVIA 120® hematology analyzer is capable of calculating the difference ("HGB Delta", or "HGBΔ") between the total and intracellular HGB concentrations (all HGB concentrations are in grams per deciliter, g/dL, of whole blood), as follows:

$$\text{HGB}\Delta, \text{g/dL} = \text{Total HGB}, \text{g/dL}_{HGB\ Channel} - \text{Intracellular HGB}, \text{g/dL}_{Red\ Cell\ Channel}$$

In the above equation, HGBΔ represents the concentration of the extracellular HGB in the blood, plasma, or serum sample. Under ordinary conditions, delta HGB (HGBΔ)=0.

Thus, according to the present invention, total hemoglobin is measured and monitored using the HGB channel of the hematology instrument, while the RBC channel detects only the intracellular HGB contained within the red blood cells of a blood sample. These two measurements are subtracted to yield the HGB Delta, which represents extracellular HGB.

In the system according to the present invention, HGB delta was introduced as a readout parameter in order to provide a check on the HGB results obtained in the HGB channel with certain types of abnormal or pathological blood samples, including lipemic and icteric blood samples and samples having elevated white blood cell counts. Such abnormal blood samples have been shown to yield artificially elevated HGB results in the H*™ System HGB channel (See, M. Malin et al., 1989, *Am. J. Clin. Path.,* 92:286–294). For example, certain blood samples scatter light, and such light scattering interference causes some of the light to be undetected. This light scattering interference causes an apparent increase, or artificial elevation, in the absorbed light, or absorbance value, for the sample. Because an HGB concentration can be obtained from the Red Blood Cell channel of a hematology analyzer (Tycko et al., 1985, *Appl. Optics,* 24:1355–1365), HGBΔ (or HGB Delta) was newly found by the present inventors to be able to be introduced as a readout parameter for the analyzer, wherein the value for intracellular hemoglobin derived from the analyzer's Red Cell channel was subtracted from the value for total hemoglobin derived from the analyzer's Hemoglobin channel to yield the HGBΔ value (g/dL in blood).

The present method of measuring and determining the intracellular versus extracellular, or exogenously added, HGB concentration in a whole blood sample, as well as the total HGB concentration, is capable of being used and performed on any of the commercially available Bayer H*™System or ADVIA 120® hematology analyzer instruments. However, it will be understood by those having skill in the pertinent art that other hematology instruments having a two channel system of measuring HGB concentration in the blood can be designed to perform the method of HGB determination and monitoring as described herein, and are embraced by the present invention. Also embraced by the present method are a series or combination of hematology analyzers which are designed and/or programmed to operate on the basis of a two channel hemoglobin analysis system.

Thus, the present invention provides a method for directly determining and monitoring extracellular hemoglobin concentration in a blood sample, preferably a whole blood sample, that is performed on an automated hematology analyzer, preferably having two analytic channels for hemoglobin measurement. The method involves the determination of the total hemoglobin concentration of a blood sample aliquot in a channel of the analyzer that is suitable for determining detecting, and/or measuring hemoglobin. By way of the present method, total hemoglobin concentrations of about 0.5–1 g/dL, or 1.1 g/dL, to about 25 g/dL of blood, preferably about 1 g/dL to about 25 g/dL, more preferably about 2 g/dL to about 25 g/dL of blood, and most preferably, about 6 g/dL to about 22 g/dL of blood are able to be determined in a blood, plasma, or serum sample, or aliquot thereof. As will be appreciated by the skilled practitioner, a normal hemoglobin value is in the range of about 11–18 g/dL of blood. For females, the normal hemoglobin range is about 11–16 g/dL of blood; for males, the normal hemoglobin range is about 13–18 g/dL of blood; and for newborns, the normal hemoglobin range is about 16–20 g/dL of blood (*Fundamentals of Clinical Chemistry,* Eds. N. Tietz, W. B. Saunders Co., 1970, p. 944). Also, by way of example, an anemic individual would typically be likely to have a hemoglobin value in the range of about 6 to about 12 g/dL of blood.

The method further involves the determination of the intracellular concentration of the blood sample aliquot in a channel of the analyzer that is suitable for determining, detecting and/or measuring red blood cells. Intracellular hemoglobin amounts that are able to be determined and measured by way of the present method include HGB concentrations of from about 0.5–1 g/dL, or 1.1 g/dL, to about 25 g/dL of blood, preferably about 1 g/dL to about 25 g/dL, more preferably about 4 g/dL to about 24 g/dL of blood and most preferably, about 5 g/dL to about 23 g/dL of blood. A most preferred range of HGB concentrations for detection is about 6 g/dL to about 18 g/dL of blood. A critical total hemoglobin concentration that is able to be measured by the method of this invention is about 6 g/dL, more preferably, 5.6 g/dL, which are concentrations of hemoglobin that are relevant to transfusions, where the decision point for transfusing a patient is approximately 6–7 g/dL of total hemoglobin.

When the total and intracellular hemoglobin concentrations have been determined, these values are used to calculate the difference between total and intracellular hemoglobin concentrations so as to arrive at the value for the extracellular hemoglobin concentration in the blood sample, a value which is calculated automatically by the hematology analyzer. According to the present invention, the red cell channel of the hematology analyzer measures the hemoglobin concentration in whole blood as follows:

$$[HGB]_{Blood,\ Red\ Cell\ Channel/Intracellular}\ (g/dL) = [CHCM\ (g/dL) \times RBC\ Count\ (cells/mm^3) \times MCV\ (femtoliters/cell)]/1000].$$

The HGB channel measures that total hemoglobin concentration, i.e., $[HGB]_{Intracellular} + [HGB]_{Extracellular}$.

In accordance with the described method, the automated hematology analyzer, e.g., ADVIA®120, calculates the difference between the Total HGB concentration and Intracellular HGB concentration to yield the HGB Delta, which corresponds to the extracellular or exogenous HGB concentration.

EXAMPLES

The following examples as set forth herein are meant to illustrate and exemplify the various aspects of carrying out the present invention and are not intended to limit the invention in any way.

Example 1

Materials and Methods

PEG HGB (Enzon, Inc., Piscataway, N.J.) was received frozen and stored frozen in the freezer. The frozen bag was thawed prior to using and was transferred into five 50 ml polypropylene test tubes. Three tubes were refrozen for later use; the other two tubes were stored in the refrigerator. An appropriate aliquot for each experiment was decanted into a test tube and was allowed to equilibrate to room temperature prior to use.

The experiments described herein were performed on a calibrated ADVIA 120®) automated hematology instrument (Bayer Corporation). The hemoglobin channel on this instrument utilized a cyanide-containing HGB reagent, such as that described in U.S. Pat. No. 5,858,794 to M. Malin, and a Red Blood Cell Diluent (RBC Diluent), as described in U.S. Pat. No. 5,817,519 to D. Zelmanovic et al. and U.S. Ser. No. 08/884,595, filed Jun. 27, 1997 to D. Zelmanovic et al.).

To calibrate the ADVIA 120® hematology system, the calibrator material (ADVIA 120® Setpoint™ calibrator) was aspirated ten times, and the mean HGB value was determined. The system calibrator factor was then set such that the mean calibrator value corresponded to the label value for HGB (g/dL) on the calibrator. To estimate the precision of the HGB channel, a freshly drawn whole blood sample was aspirated twenty times and the mean and standard deviation (SD) were calculated. Acceptable precision was as follows: SD≦0.11 g/dL.

Blood samples obtained from normal volunteers were anticoagulated, preferably using $K_3EDTA$ (≅12.15 mg/tube).

Most of the experiments described in the examples herein were performed at HGB concentration levels of approximately 6 g/dL, since PEG-HGB (Enzon, Inc.) is reported to contain 6 g/dL of bovine hemoglobin. The recovered HGB value was 5.4±2 g/dL, which correlated well with the nominal value 6 g/dL of blood. In addition, in all of the examples utilizing a Bayer Corporation hematology analyzer, the hemoglobin precision of the instrument was checked prior to calibration by twice aspirating PEG-HGB prior to each experiment.

Example 2

To determine the recovery of added hemoglobin in a plasma sample, the experiment described in Example 2 was performed. In this experiment, variable volumes of PEG hemoglobin (Enzon, Inc.) were added to plasma, which was analyzed on a Bayer ADVIA 120® hematology instrument, so as to assess the variation of exogenous PEG-HGB in plasma.

Ten tubes containing aliquots of a normal blood sample collected in ethylenediaminetetraacetic acid, EDTA ("normal EDTA whole blood"), were centrifuged at 750×g. The plasma was removed and then re-centrifuged to yield cell-free plasma. Into each of seven tubes were added the amounts of plasma and PEG HGB as indicated in Table 1 to yield a final volume of 4.0 ml in each tube. Each tube was aspirated four times to determine replicate values.

is consistent with the presence of PEG-HGB entirely as extracellular hemoglobin. In addition, the recovery was linear in accordance with the experimental design. All HGB levels met the linearity specifications of 0.2 g/dL or 2% of the expected values.

Example 3

In this example, experiments were performed in which a constant concentration of hemoglobin was added into a whole blood matrix in which the total hemoglobin was varied, as measured from the HGB channel of the hematology analyzer.

Ten tubes of normal EDTA whole blood were centrifuged at 750×g. Cell-free plasma was removed and the red blood cells were pooled. An aliquot of red blood cells was removed and plasma was added so that the total hemoglobin concentration was 10 g/dL, i.e., approximately 6 ml of packed red blood cells plus 14 ml of plasma). The total volume of the 10 g/dL aliquot needed was 15 ml. To each of six tubes, the volumes of the 10 g/dL aliquot and the cell-free plasma were added in the amounts shown in Table 3 to produce hemoglobin (HGB) values of 6.0, 5.0, 4.0, 3.0, 2.0 and 1.0 g/dL.

TABLE 2

| "A" Samples | mL of Whole Blood* | mL Plasma | Cellular HGB g/dL |
|---|---|---|---|
| 1A | 3.0 | 2.0 | 6.0 |
| 2A | 2.5 | 2.5 | 5.0 |
| 3A | 2.0 | 3.0 | 4.0 |
| 4A | 1.5 | 3.5 | 3.0 |
| 5A | 1.0 | 4.0 | 2.0 |
| 6A | 0.5 | 4.5 | 1.0 |

*In Table 2, whole blood contained HGB at 10.0 g/dL.

Two ml of the "A" samples of Table 2 were diluted with 2 ml of PEG-HGB. Because an equal volume of PEG-HGB

TABLE 1

Recovery of Exogenous Hemoglobin

| Plasma (ml) | PEG-HGB (ml) | Measured Total HGB* | Measured RBC HGB | Measured HGB Delta | Predicted HGB Delta | Difference: (Measured HGBΔ Minus Predicted HGBΔ) |
|---|---|---|---|---|---|---|
| 4.0 | 0 | 0.0 | 0.0 | 0.0 | 0.0 | 0.0 |
| 3.6 | 0.4 | 0.5 0.00 | 0.0 0.00 | 0.5 0.00 | 0.6 | 0.1 |
| 3.2 | 0.8 | 1.0 0.00 | 0.0 0.00 | 1.0 0.00 | 1.1 | 0.1 |
| 2.4 | 1.6 | 2.2 0.05 | 0.0 0.00 | 2.2 0.05 | 2.2 | 0 |
| 1.6 | 2.4 | 3.4 0.05 | 0.0 0.00 | 3.4 0.05 | 3.4 | 0 |
| 0.8 | 3.2 | 4.4 0.10 | 0.0 0.00 | 4.5 0.10 | 4.5 | 0 |
| 0 | 4.0 | 5.6 0.00 | 0.0 0.00 | 5.6 0.00 | 5.6 | 0 |

*The data presented in Table 1 represent the means of four replicates.

The four replicate HGB values were averaged and the percent difference between the expected and observed results was calculated (see Table 1).

The results of these replicate experiments show that exogenously added hemoglobin, i.e., PEG-HGB (Enzon, Inc.) was detected from the hemoglobin channel, and not from the RBC channel of the automated hematology analyzer instrument, based on the output profile. (Table 1). This was added to an equal volume of each aliquot (i.e., 6.0 g/dL, 5.0 g/dL, 4.0 g/dL, 3.0 g/dL, 2.0 g/dL and 1.0 g/dL), both the cellular HGB and the extracellular HGB of each aliquot were reduced by 50%. The PEG-HGB, which undiluted is at a concentration of 5.6 g/dL, was thus reduced to 2.8 g/dL in each aliquot. The total HGB was equal to the sum of the extracellular PEG-HGB plus the cellular HGB. Each tube was aspirated five times for replicate results.

TABLE 3

| "B" Samples | ml of "A" Sample* | PEG-HGB (ml) | Total HGB (g/dL)** Predicted | Total HGB (g/dL)** Assayed | Calculated HGB (g/dL) (i.e., cellular HGB) Predicted | Calculated HGB (g/dL) (i.e., cellular HGB) Assayed | HGB Delta (g/dL) (i.e. extracellular HGB) Predicted | HGB Delta (g/dL) (i.e. extracellular HGB) Assayed |
|---|---|---|---|---|---|---|---|---|
| 1B | 2.0 | 2.0 | 5.8 | 5.8 ± 0.09 | 3.0 | 3.2 ± 0.05 | 2.8 | 2.6 ± 0.11 |
| 2B | 2.0 | 2.0 | 5.3 | 5.4 ± 0.05 | 2.5 | 2.7 ± 0.05 | 2.8 | 2.7 ± 0.08 |
| 3B | 2.0 | 2.0 | 4.8 | 4.9 ± 0.08 | 2.0 | 2.2 ± 0.08 | 2.8 | 2.7 ± 0.11 |
| 4B | 2.0 | 2.0 | 4.3 | 4.3 ± 0.08 | 1.5 | 1.7 ± 0.04 | 2.8 | 2.8 ± 0.07 |
| 5B | 2.0 | 2.0 | 3.8 | 3.8 ± 0.04 | 1.0 | 1.1 ± 0.05 | 2.8 | 2.8 ± 0.05 |
| 6B | 2.0 | 2.0 | 3.3 | 3.4 ± 0.0 | 0.5 | 0.5 ± 0.04 | 2.8 | 2.9 ± 0.04 |

*The "A" samples were prepared according to Table 3. Undiluted PEG-HGB contained 5.6 g/dL of assayable Hemoglobin.
**All data points are the mean ± SD of 5 replicates.

The results presented in Table 3 in this example show that when a constant concentration of extracellular PEG-HGB was added to a whole blood matrix in which the intracellular HGB concentration varied, there was an acceptable recovery of both extracellular PEG-HGB and cellular HGB. The results in Table 3 indicate that the amount of PEG-HGB was recoverable and measurable on the Bayer ADVIA 120® instrument when PEG-HGB was added to low cellular HGB whole blood samples. In view of the acceptable performance of the present method for recovering values of exogenous HGB, as well as cellular HGB, in human blood samples spiked with PEG-HGB, the method provides similar applicability for use with transfused patients' blood, plasma, or serum samples, especially whole blood samples, containing added cell-free HGB derivatives or oxygen-carrying HGB substitutes, as described above.

Example 4

This example presents data showing the stability of exogenously added PEG-HGB in whole blood samples. Samples were prepared by the addition of variable volumes of whole blood (6.0 g/dL HGB) to variable volumes of PEG-HGB (5.6 g/dL), (Table 4A). Each sample was aspirated four times. The samples were assayed 1 hour after preparation and then 24 hours later after refrigerated storage at 5° C. (Table 4B).

From these experiments it was demonstrated that the PEG-HGB hemoglobin substitute was recoverable after 24 hours when blood samples were stored at 2–8° C. As shown in Tables 4A and 4B, there was virtually no change in Total HGB, Calculated HGB (i.e., cellular HGB), or HGB Delta (i.e., extracellular HGB) in blood samples stored at 2–8° C. for 24 hours (Table 4B), from the values at time zero (Table 4A). Thus, provided that the red cell count is stable during storage, the HGB Delta, due to the presence of PEG-HGB, was also constant after storage for 24 hours at 2–8° C.

TABLE 4A

Time Zero

| Whole Blood (ml) | PEG-HGB (ml) | Predicted Total HGB | Total HGB | Calc. HGB (cellular) | HGB Delta (extra-cellular) |
|---|---|---|---|---|---|
| 0.0 | 0.0 | 0.0* | 0.0 ± 0.00 | 0.0 ± 0.00 | 0.0 ± 0.00 |
| 0.0 | 4.0 | 5.6 | 5.4 ± 0.05 | 0.0 ± 0.0 | 5.4 ± 0.05 |
| 0.8 | 3.2 | 5.7 | 5.5 ± 0.13 | 1.2 ± 0.00 | 4.3 ± 0.13 |
| 1.6 | 2.4 | 5.8 | 5.7 ± 0.08 | 2.5 ± 0.05 | 3.2 ± 0.13 |
| 2.4 | 1.6 | 5.8 | 5.9 ± 0.1 | 3.7 ± 0.00 | 2.2 ± 0.05 |
| 3.2 | 0.8 | 5.9 | 6.1 ± 0.06 | 4.9 ± 0.00 | 1.2 ± 0.06 |
| 3.6 | 0.4 | 6.0 | 6.2 ± 0 | 5.5 ± 0.06 | 0.8 ± 0.06 |
| 4.0 | 0.0 | 6.0 | 6.2 ± 0.05 | 6.0 ± 0.05 | 0.2 ± 0.08 |

*This sample was pure plasma.

TABLE 4B*

24 hours/2–8° C.

| Total HGB | Calc HGB (cellular) | HGB Delta (extra-cellular) |
|---|---|---|
| 0.0 ± 0.00 | 0.0 ± 0.00 | 0.0 ± 0.00 |
| 5.4 ± 0.05 | 0.0 ± 0.05 | 5.4 ± 0.05 |
| 5.6 ± 0.0 | 1.2 ± 0.00 | 4.4 ± 0.05 |
| 5.7 ± 0.00 | 2.5 ± 0.05 | 3.3 ± 0.05 |
| 5.9 ± 0.00 | 3.7 ± 0.05 | 2.2 ± 0.05 |
| 6.1 ± 0.06 | 4.9 ± 0.05 | 1.1 ± 0.05 |
| 6.2 ± 0.05 | 5.5 ± 0.05 | 0.7 ± 0.05 |
| 6.1 ± 0.06 | 5.9 ± 0.05 | 0.2 ± 0.06 |

*All data points in Tables 4A and 4B represent the mean ± the SD of 4 replicates.

Example 5

This example describes the analytical measurement of another oxygen carrying blood substitute, namely, a cell-free, glutaraldehyde-polymerized hemoglobin based oxygen carrier (HBOC), Hemopure®, obtained from Biopure Corporation (Cambridge, Mass.), as performed according to the present invention on an ADVIA 120® hematology instrument (Bayer Corporation). Hemopure® is bovine hemoglobin, polymerized with glutaraldehyde to produce oligomers with a MW of 500,000. Polymerization was designed into this product to decrease the kidney excretion rate.

Two types of experiments were performed and described using the Hemopure® product: (1) Hemopure® was spiked into human plasma, and (2) Hemopure® was spiked into human whole blood prior to automated hematology analysis and the determination of exogenous hemoglobin concentration.

The experiments measuring Hemopure® as an exogenous hemoglobin substance in a blood or plasma sample were carried out as described in the above examples using the ADVIA 120® automated hematology analyzer. In accordance with this invention, the ADVIA 120® analyzer calculates the difference between the Total hemoglobin and the RBC intracellular hemoglobin concentrations to yield Hemoglobin Delta (i.e., exogenous hemoglobin).

Recovery of HBOC Exogenous HGB (Hemopure®) in Cell-Free Plasma

Plasma was obtained from fresh human blood by centrifugation for 25 minutes in a Sorvall R-3$^R$ centrifuge equipped with an HB4L horizontal bucket rotor at 2400 rpm (620×g). The plasma supernatant was re-centrifuged for 10 minutes at 620×g and the pellet was excluded. Cell-free plasma was distributed in glass tubes as follows: 5.00, 4.75, 4.50, 3.00, 2.00, 1.00 and 0.00 ml. Into these tubes was added the Hemopure® product, as follows: 0.00, 0.25, 0.50, 1.00, 2.00, 3.00, 4.00 and 5.00 ml, respectively, so that the total volume was 5.00 ml. The tubes were capped and mixed by inversion (10 times), and then were assayed 30–60 minutes later on ADVIA 120®, using 5 replicates per tube. The total HGB, intracellular HGB and HGB Delta concentrations were tabulated.

The results are summarized in Table 5, wherein the assayed results are the means of 5 replicates. For the Hemopure® product, the difference between HGB Delta$_{predicted}$ and HGB Delta$_{assayed}$ was zero or 0.1, and was therefore within the ADVIA 120® analyzer's HGB linearity specification of 0.2 g/dL, or 2% relative difference. For all levels, the intracellular HGB concentration was zero, as required by the experimental design. The data illustrate that recovery of exogenous HGB is linear in a plasma matrix over the range of 0.6 to 13.0 g/dL.

TABLE 5

Recovery of Exogenous Hemoglobin (HGB), ("Hemopure ®") in Plasma

| % volume of Exogenous HGB | Plasma (ml) | Hemopure ® (ml) | Total HGB (g/dL) Predicted | Total HGB (g/dL) Assayed | HGB Delta (g/dL) Predicted | HGB Delta (g/dL) Assayed | Difference Measured HGBΔ-Predicted HGBΔ |
|---|---|---|---|---|---|---|---|
| 0% | 5.0 | 0.0 | 0.0 | 0.0 ± 0.00 | 0.0 | 0.0 ± 0.00 | 0.0 |
| 5% | 4.75 | 0.25 | 0.7 | 0.6 ± 0.05 | 0.7 | 0.6 ± 0.05 | −0.05 |
| 10% | 4.5 | 0.5 | 1.3 | 1.2 ± 0.00 | 1.3 | 1.2 ± 0.00 | −0.1 |
| 20% | 4.0 | 1.0 | 2.6 | 2.5 ± 0.05 | 2.6 | 2.5 ± 0.05 | −0.1 |
| 40% | 3.0 | 2.0 | 5.2 | 5.2 ± 0.04 | 5.2 | 5.2 ± 0.04 | 0.0 |
| 60% | 2.0 | 3.0 | 7.8 | 7.8 ± 0.00 | 7.8 | 7.8 ± 0.00 | 0.0 |
| 80% | 1.0 | 4.0 | 10.4 | 10.4 ± 0.04 | 10.4 | 10.4 ± 0.00 | 0.0 |
| 100% | 0.0 | 5.0 | 13.0 | 13.0 ± 0.08 | 13.0 | 13.0 ± 0.08 | 0.0 |

Recovery of HBOC Exogenous HGB (Hemopure®) in Whole Blood

Whole blood, obtained from volunteers and anticoagulated in K$_3$EDTA, was manipulated so that the total HGB concentration was 13.0 g/dL. Whole blood was distributed in glass tubes as follows: 5.00, 4.75, 4.50, 4.00, 3.00, 2.00, 1.00 and 0.00 ml. Into these tubes, Hemopure® was added as follows: 0.00, 0.25, 0.50, 1.00, 2.00, 3.00, 4.00 and 5.00 ml, respectively, so that the total volume was 5.00 ml. The tubes were capped and mixed by inversion (10 times), and then were assayed 30–60 minutes later on ADVIA 120®, using 5 replicates per tube. The total HGB, intracellular HGB and HGB Delta concentrations were tabulated.

Using whole blood and Hemopure®, intracellular HGB concentration decreased as extracellular HGB increased. The results are summarized in Table 6, in which the assayed results are the means of 5 replicates. For the Hemopure® product, the difference between HGB Delta$_{predicted}$ and HGB Delta$_{assayed}$ was generally zero or 0.1, and did not exceed the ADVIA 120® analyzer's HGB linearity specification. For all levels, the intracellular HGB concentration was zero, as required by the experimental design. The data illustrated that recovery of exogenous HGB was linear in a whole blood matrix over the range of 0.09 to 13.0 g/dL.

TABLE 6

Recovery of Exogenous Hemoglobin (HGB), ("Hemopure ®") in Whole Blood

| % volume of Exogenous HGB | Whole Blood (ml) | Hemopure ® (ml) | Total HGB (g/dL) | | Cellular HGB (g/dL) | | HGB Delta (g/dL) | | Difference Measured HGBΔ-Predicted HGBΔ |
|---|---|---|---|---|---|---|---|---|---|
| | | | Predicted | Assayed | Predicted | Assayed | Predicted | Assayed | |
| 0% | 5.0 | 0.0 | 13.0 | 12.9 ± 0.07 | 13.0 | 12.9 ± 0.05 | 0.0 | 0.0 ± 0.08 | 0.0 |
| 10% | 4.5 | 0.5 | 13.0 | 12.9 ± 0.05 | 11.7 | 11.7 ± 0.07 | 1.3 | 1.2 ± 0.09 | 0.1 |
| 20% | 4.0 | 1.0 | 13.0 | 12.9 ± 0.05 | 10.4 | 10.3 ± 0.09 | 2.6 | 2.6 ± 0.08 | 0.0 |
| 40% | 3.0 | 2.0 | 13.0 | 12.9 ± 0.1 | 7.8 | 7.8 ± 0.04 | 5.2 | 5.1 ± 0.04 | 0.1 |
| 60% | 2.0 | 3.0 | 13.0 | 13.0 ± 0.00 | 5.2 | 5.2 ± 0.04 | 7.8 | 7.8 ± 0.05 | 0.0 |
| 80% | 1.0 | 4.0 | 13.0 | 13.0 ± 0.11 | 2.6 | 2.7 ± 0.04 | 10.4 | 10.3 ± 0.1 | 0.1 |
| 100% | 0.0 | 5.0 | 13.0 | 12.9 ± 0.09 | 0.0 | 0.0 ± 0.00 | 13.0 | 12.9 ± 0.09 | 0.0 |

Example 6

This example describes the analytical measurement of a another cell-free oxygen carrying blood substitute, Oxyglobin, (Biopure Corporation, Cambridge, Mass.), performed according to the present invention on an ADVIA 120® hematology instrument (Bayer Corporation). Like Hemopure®, Oxyglobin is also a cell-free solution of glutaraldehyde-polymerized hemoglobin.

As in Example 5, two types of experiments were performed using the Oxyglobin product: (1) Oxyglobin was spiked into human plasma, and (2) Oxyglobin was spiked into human whole blood prior to automated hematology analysis.

The experiments measuring Oxyglobin as an exogenous hemoglobin substance in a blood or plasma sample were carried out as described in the above examples using the ADVIA 120® automated hematology analyzer.

Recovery of Oxyglobin in Cell-Free Plasma

Plasma was obtained from fresh human blood by centrifugation for 25 minutes in a Sorvall R-3$^R$ centrifuge equipped with an HB4L horizontal bucket rotor at 2400 rpm (620×g). The plasma supernatant was re-centrifuged for 10 minutes at 620×g and the pellet was excluded. Cell-free plasma was distributed in glass tubes as follows: 5.00, 4.75, 4.50, 3.00, 2.00, 1.00 and 0.00 ml. Oxyglobin was added to these tubes as follows: 0.00, 0.25, 0.50, 1.00, 2.00, 3.00, 4.00 and 5.00 ml, respectively, so that the total volume was 5.00 ml. The tubes were capped and mixed by inversion (10 times), and then were assayed 30–60 minutes later on the ADVIA 120® hematology analyzer, using 5 replicates per tube. The total HGB, intracellular HGB and HGB Delta concentrations were tabulated.

The results are summarized in Table 7, wherein the assayed results are the means of 5 replicates. As observed for the Hemopure® product (Example 5), the difference between HGB Delta$_{predicted}$ and HGB Delta$_{assayed}$ for Oxyglobin was zero or 0.1, and was therefore within the ADVIA 120® analyzer's HGB linearity specification of 0.2 g/dL, or 2% relative difference. For all levels, the intracellular HGB concentration was zero, as required by the experimental design. The data illustrated that recovery of exogenous HGB was linear in a plasma matrix over the range of 0.6 to 13.0 g/dL.

TABLE 7

Recovery of Exogenous Hemoglobin (HGB), (Oxyglobin) in Plasma

| % volume of Exogenous HGB | Plasma (ml) | Oxyglobin (ml) | Total HGB (g/dL) | | HGB Delta (g/dL) | | Difference Measured HGBΔ-Predicted HGBΔ |
|---|---|---|---|---|---|---|---|
| | | | Predicted | Assayed | Predicted | Assayed | |
| 0% | 5.0 | 0.0 | 0.0 | 0.0 ± 0.00 | 0.0 | 0.0 ± 0.00 | 0.0 |
| 5% | 4.75 | 0.25 | 0.7 | 0.6 ± 0.00 | 0.7 | 0.6 ± 0.00 | −0.1 |
| 10% | 4.5 | 0.5 | 1.3 | 1.3 ± 0.00 | 1.3 | 1.3 ± 0.00 | 0.0 |
| 20% | 4.0 | 1.0 | 2.6 | 2.6 ± 0.04 | 2.6 | 2.6 ± 0.04 | 0.0 |
| 40% | 3.0 | 2.0 | 5.2 | 5.2 ± 0.05 | 5.2 | 5.2 ± 0.05 | 0.0 |
| 60% | 2.0 | 3.0 | 7.9 | 7.8 ± 0.04 | 7.8 | 7.8 ± 0.04 | 0.0 |
| 80% | 1.0 | 4.0 | 10.5 | 10.5 ± 0.05 | 10.4 | 10.5 ± 0.05 | 0.1 |

TABLE 7-continued

Recovery of Exogenous Hemoglobin (HGB), (Oxyglobin) in Plasma

| % volume of Exogenous HGB | Plasma (ml) | Oxyglobin (ml) | Total HGB (g/dL) | | HGB Delta (g/dL) | | Difference Measured HGBΔ-Predicted HGBΔ |
|---|---|---|---|---|---|---|---|
| | | | Predicted | Assayed | Predicted | Assayed | |
| 100% | 0.0 | 5.0 | 13.1 | 13.1 ± 0.11 | 13.0 | 13.1 ± 0.11 | 0.1 |

Recovery of Oxyglobin in Whole Blood

Whole blood, obtained from volunteers and anticoagulated in $K_3$EDTA, was manipulated so that the total HGB concentration was 13.0 g/dL. Whole blood was distributed in glass tubes as follows: 5.00, 4.75, 4.50, 4.00, 3.00, 2.00, 1.00 and 0.00 ml. Oxyglobin (Biopure, Cambridge, Mass.) was added to the tubes as follows: 0.00, 0.25, 0.50, 1.00, 2.00, 3.00, 4.00 and 5.00 ml, respectively, so that the total volume in each tube was 5.00 ml. The tubes were capped and mixed by inversion (10 times), and then were assayed 30–60 minutes later on ADVIA 120®, using 5 replicates per tube. The total HGB, intracellular HGB and HGB Delta concentrations were tabulated.

Using whole blood and the Oxyglobin product, intracellular HGB concentration decreased as extracellular HGB increased. The results are summarized in Table 8, in which the assayed results are the means of 5 replicates. Similar to the results observed for the Hemopure® product, the difference between HGB Delta$_{predicted}$ and HGB Delta$_{assayed}$ was generally zero or 0.1 for Oxyglobin, and did not exceed the ADVIA 120® analyzer's HGB linearity specification. For all levels, the intracellular HGB concentration was zero, as required by the experimental design. The data illustrate that recovery of exogenous HGB is linear in a whole blood matrix over the range of 0.09 to 13.0 g/dL.

automated hematology analyzer such as the Bayer Corporation ADVIA 120® Hematology Analyzer. The ADVIA 120® analyzer was able to directly and quantitatively detect the Hemopure® and Oxyglobin materials in plasma and whole blood over a range of 0.6 to 13.0 g/dL. The ADVIA 120® reported these hemoglobin substitutes as extracellular hemoglobin.

As described herein and according to the operation of the automated hematology analyzer in accordance with the present invention, the hemoglobin channel calorimetrically measures the total HGB concentration in the sample by interaction of HGB in the same with ionic cyanide in the presence of surfactant micelles. (See, M. J. Malin et al., 1992, *J. Anal. Chim. Acta.*, 262:67–77 and M. J. Malin et al., 1989, *J. Amer. Clin. Path.*, 92:286–294). Thus, total HGB is a combination of intracellular HGB and extracellular HGB. In contrast, the RBC channel typically registers only the intracellular HGB present in a sample. The automated system calculates the concentration of extracellular HGB by obtaining the difference between the total and the intracellular HGB levels. Both materials were recovered within specification in a linearity experiment in matrices of plasma and whole blood.

Example 7

Absorption spectra in water confirmed that the Hemopure® and Oxyglobin materials (Biopure, Cambridge,

TABLE 8

Recovery of Exogenous Hemoglobin (HGB), (Oxyglobin), in Whole Blood

| % volume of Exogenous HGB | Whole Blood (ml) | Oxyglobin (ml) | Total HGB (g/dL) | | Cellular HGB (g/dL) | | HGB Delta (g/dL) | | Difference Measured HGBΔ-Predicted HGBΔ |
|---|---|---|---|---|---|---|---|---|---|
| | | | Predicted | Assayed | Predicted | Assayed | Predicted | Assayed | |
| 0% | 5.0 | 0.0 | 13.0 | 13.0 ± 0.05 | 13.0 | 13.0 ± 0.10 | 0.0 | 0.0 ± 0.13 | 0.0 |
| 5% | 4.75 | 0.25 | 13.0 | 12.9 ± 0.11 | 12.4 | 12.5 ± 0.11 | 0.6 | 0.4 ± 0.08 | -0.2 |
| 10% | 4.5 | 0.5 | 13.0 | 13.0 ± 0.04 | 11.7 | 11.8 ± 0.09 | 1.3 | 1.2 ± 0.09 | -0.1 |
| 20% | 4.0 | 1.0 | 13.0 | 13.1 ± 0.04 | 10.4 | 10.6 ± 0.07 | 2.6 | 2.5 ± 0.07 | -0.1 |
| 40% | 3.0 | 2.0 | 13.0 | 13.2 ± 0.1 | 7.8 | 8.0 ± 0.04 | 5.2 | 5.2 ± 0.08 | 0.0 |
| 60% | 2.0 | 3.0 | 13.0 | 13.1 ± 0.09 | 5.2 | 5.3 ± 0.05 | 7.8 | 7.8 ± 0.08 | 0.0 |
| 80% | 1.0 | 4.0 | 13.0 | 13.1 ± 0.05 | 2.6 | 2.7 ± 0.13 | 10.4 | 10.4 ± 0.15 | 0.0 |
| 100% | 0.0 | 5.0 | 13.0 | 13.0 ± 0.09 | 0.0 | 0.0 ± 0.00 | 13.0 | 13.0 ± 0.09 | 0.0 |

The results of the experiments described in Examples 5 and 6 demonstrate that the oxygen carrying blood substitutes Hemopure® and Oxyglobin (Biopure, Cambridge, Mass.) could be quantitatively detected in a direct manner by an Mass.) were hemoglobin derivatives in which the heme groups were capable of oxygenation. More specifically, Hemopure®, Oxyglobin and whole blood were diluted 251-fold in MilliQ distilled water; mixed, and scanned from 750 to 450 nm versus distilled water on a Cary 3 Spectrophotometer. The spectra of whole blood and the two blood substitutes exhibited spectral maxima at 541 nm and 577 nm, respectively, and spectral minima at 508 nm and 560 nm, respectively. These features are characteristic of those of oxyhemoglobin (van Kampen and Ziljstra, 1965, *Adv. Clin. Chem.*, 8:141) when compared with whole blood. Because the Hemopure® and Oxyglobin products have a spectrum of oxyhemoglobin in oxygenated water, the heme iron is in the ferrous oxidation state, as it is in whole blood hemoglobin.

Example 8

Both the Hemopure® and the Oxyglobin (Biopure, Cambridge, Mass.) products behaved like hemoglobin in whole blood when diluted 251-fold with a cyanide-containing hemoglobin reagent and analyzed on the ADVIA 120® hematology analyzer. Specifically, 20 µl of Hemopure® and Oxyglobin were each diluted into 5.0 ml of cyanide containing hemoglobin reagent as used on the ADVIA 120® analyzer. The samples were mixed and then scanned from 750 nm to 450 nm on a Cary 3 spectrophotometer and compared with reagent in 1 cm pathlength cuvettes. $A_{750}$ was set to zero. As a control, an aliquot of fresh human blood was treated as described above for the test products. The results are summarized in Table 9 which shows the spectral maxima and minima of the hemoglobin based oxygen carriers and whole blood in the cyanide-containing hemoglobin reagent.

TABLE 9

| Sample | $A_{550}$ nm | $A_{514}$ nm | $A_{550} / A_{514}$ |
|---|---|---|---|
| Whole blood | 0.3239 | 0.2236 | 1.45 |
| Hemopure ® | 0.3267 | 0.2331 | 1.40 |
| Oxyglobin | 0.3423 | 0.2453 | 1.40 |

The data show that both of the Biopure HBOC's resembled human blood with respect to their reaction with the cyanide-containing hemoglobin reagent. All spectra exhibited a maximum at 550 nm and a minimum at 514 nm, with a similar max/min absorbance ratio. This experiment demonstrates that both the Hemopure® and the Oxyglobin products contain heme, since the product obtained in the HGB reagent is micellized dicyano-$Fe^{+3}$ protoporphyrin IX (see, M. Malin et al., 1992, *Anal. Chim. Acta*, 262:67–77).

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method for the determination, quantification and monitoring of extracellular hemoglobin in a whole blood, plasma or serum sample performed on an automated hematology analyzer having at least two analytic channels for hemoglobin measurement, comprising:

(a) determining total hemoglobin concentration in an aliquot of the sample in a hemoglobin analytic channel of the analyzer;

(b) determining cellular hemoglobin concentration in the sample aliquot in a red blood cell analytic channel of the analyzer; and (c) calculating the difference between the total hemoglobin concentration determined from the hemoglobin analytic channel and the cellular hemoglobin concentration determined from the red blood cell analytic channel of the analyzer to yield the extracellular hemoglobin concentration in the whole blood, plasma, or serum sample.

2. The method according to claim 1, wherein the sample is a normal whole blood sample.

3. The method according to claim 1, wherein the sample is an abnormal whole blood sample.

4. The method according to claim 3, wherein the abnormal whole blood sample is derived from an individual having a pathological condition.

5. The method according to claim 4, wherein the pathological condition is selected from the group consisting of blood loss during surgery, blood loss during trauma, and hemorrhagic shock.

6. The method according to claim 1, wherein the sample is a plasma or serum sample.

7. The method according to claim 1, wherein the total hemoglobin concentration in step (a) is from about 0.5 g/dL to about 25 g/dL of blood, plasma, or serum.

8. The method according to claim 7, wherein the total hemoglobin concentration in step (a) is from about 6 g/dL to about 22 g/dL of blood, plasma, or serum.

9. The method according to claim 1, wherein the cellular hemoglobin concentration in step (b) is from about 0.5 g/dL to about 25 g/dL of blood, plasma, or serum.

10. The method according to claim 9, wherein the cellular hemoglobin concentration in step (b) is from about 4 g/dL to about 24 g/dL of blood, plasma, or serum.

11. The method according to claim 10, wherein the cellular hemoglobin concentration is about 6.0 g/dL of blood, plasma, or serum.

12. The method according to claim 1, wherein the hemoglobin analytic channel of step a) measures the total hemoglobin concentration in the sample by hemolysis and extraction of hemes from their biological complex with globin by forming a ligated ferric heme species capturable in a surfactant micelle.

13. The method according to claim 1, wherein the red blood cell analytic channel of step b) measures red cell concentration, red cell volume, and hemoglobin concentration of individual red blood cells as they pass through two light scattering detectors virtually one cell at a time.

14. The method according to claim 1, wherein the total hemoglobin concentration of step (a) is determined from calorimetric absorbance in the hemoglobin analytic channel of the analyzer.

15. The method according to claim 1, wherein the cellular hemoglobin concentration of step (b) is determined by the formula:

$$RBC \times MCV \times CHCM/1000;$$

wherein RBC is a red blood cell cytogram value in the red blood cell analytic channel of the hematology analyzer; MCV is mean cell volume; and CHCM is cellular hemoglobin concentration mean obtained from the red blood cell analytic channel of the hematology analyzer.

16. The method according to claim 1, wherein the extracellular hemoglobin in the sample is due to the presence of a cell-free hemoglobin product or an oxygen-carrying hemoglobin substitute in the blood, plasma or serum.

17. The method according to claim 16, wherein the cell-free hemoglobin product or the oxygen-carrying hemoglobin substitute is selected from the group consisting of purified hemoglobin, recombinant hemoglobin, cross-linked hemoglobin, polymerized hemoglobin and hemoglobin coupled to polyethylene glycol (PEG-HGB).

18. The method according to claim 17, wherein the purified hemoglobin is purified bovine hemoglobin or purified human hemoglobin.

19. The method according to claim 17, wherein the recombinant hemoglobin is recombinant human hemoglobin.

20. An automated method for the determination, quantification and monitoring of extracellular hemoglobin in a whole blood, plasma or serum sample performed on an automated hematology analyzer having at least two analytic channels for hemoglobin measurement, comprising:
(a) determining total hemoglobin concentration in an aliquot of the whole blood, plasma, or serum sample in a hemoglobin analytic channel of the analyzer, wherein said hemoglobin analytic channel measures the total hemoglobin concentration in the sample by hemolysis and extraction of hemes from their biological complex with globin by forming a ligated ferric heme species capturable in a surfactant micelle, and further wherein the total hemoglobin concentration is determined from calorimetric absorbance in the hemoglobin analytic channel of the analyzer;
(b) determining cellular hemoglobin concentration in the sample aliquot in a red blood cell analytic channel of the analyzer, wherein the red blood cell analytic channel measures red cell concentration, red cell volume and hemoglobin concentration of individual red blood cells as they pass through two light scattering detectors virtually one cell at a time; and
(c) calculating the difference between the total hemoglobin concentration determined from the hemoglobin analytic channel and the cellular hemoglobin concentration determined from the red blood cell analytic channel of the analyzer to yield the extracellular hemoglobin concentration in the whole blood, plasma, or serum sample.

21. The method according to claim 20, wherein the sample is a normal whole blood sample or an abnormal whole blood sample.

22. The method according to claim 21, wherein the abnormal blood sample is derived from an individual having a pathological condition.

23. The method according to claim 22, wherein the pathological condition is selected from the group consisting of blood loss during surgery, blood loss during trauma, and hemorrhagic shock.

24. The method according to claim 20, wherein the sample is a plasma or serum sample.

25. The method according to claim 20, wherein the total hemoglobin concentration in step (a) is from about 0.5 g/dL to about 25 g/dL of blood, plasma, or serum; and the cellular hemoglobin concentration in step (b) is from about 0.5 g/dL to about 25 g/dL of blood, plasma, or serum.

26. The method according to claim 25, wherein the cellular hemoglobin concentration is about 6.0 g/dL.

27. The method according to claim 20, wherein the extracellular hemoglobin in the sample is due to the presence of a cell-free hemoglobin product or an oxygen-carrying hemoglobin substitute in the blood, plasma or serum.

28. The method according to claim 27, wherein the cell-free hemoglobin product or the oxygen-carrying hemoglobin substitute is selected from the group consisting of purified hemoglobin, recombinant hemoglobin, cross-linked hemoglobin, polymerized hemoglobin, purified bovine hemoglobin and hemoglobin coupled to polyethylene glycol (PEG-HGB).

29. The method according to claim 28, wherein the purified hemoglobin is purified bovine hemoglobin or purified human hemoglobin.

30. The method according to claim 28, wherein the recombinant hemoglobin is recombinant human hemoglobin.

31. The method according to claim 20, wherein the cellular hemoglobin concentration of step (b) is determined by the formula:

$$RBC \times MCV \times CHCM/1000;$$

wherein RBC is a red blood cell cytogram value in the red blood cell analytic channel of the hematology analyzer; MCV is mean cell volume; and CHCM is cellular hemoglobin concentration mean obtained from the red blood cell analytic channel of the hematology analyzer.

* * * * *